United States Patent [19]

Hoeksema

[11] 4,154,938
[45] May 15, 1979

[54] PYRIDINE COMPOUNDS

[75] Inventor: Herman Hoeksema, Kalamazoo, Mich.

[73] Assignee: The Upjohn Company, Kalamazoo, Mich.

[21] Appl. No.: 938,689

[22] Filed: Aug. 31, 1978

Related U.S. Application Data

[60] Division of Ser. No. 874,767, Feb. 6, 1978, which is a continuation-in-part of Ser. No. 793,785, May 5, 1977, abandoned.

[51] Int. Cl.$^2$ .......................................... C07D 405/14
[52] U.S. Cl. .................................................... 546/269
[58] Field of Search ................... 260/295 PA, 294.8 C, 260/294.9

[56] References Cited

U.S. PATENT DOCUMENTS 3,335,057  8/1967  Johnson et al. ...................... 424/119

Primary Examiner—Richard Raymond
Attorney, Agent, or Firm—Roman Saliwanchik

[57] ABSTRACT

Disclosed are degradation products of the antibiotics rubradirin and rubradirin B and processes for their preparation. Some of these products have antibacterial activity, and, thus, can be used in various environments to inhibit susceptible bacteria. Also, some of these products can be used as intermediates to make useful antibacterials.

2 Claims, No Drawings

PYRIDINE COMPOUNDS

CROSS REFERENCE TO RELATED APPLICATION

This is a division of application Ser. No. 874,767, filed Feb. 6, 1978, which in turn is a continuation-in-part of application Ser. No. 793,785, filed May 5, 1977, now abandoned.

BACKGROUND OF THE INVENTION

The antibiotic rubradirin, and a microbiological process for preparing the same, are disclosed in U.S. Pat. No. 3,335,057. The structure of rubradirin has been tentatively determined to be as follows:

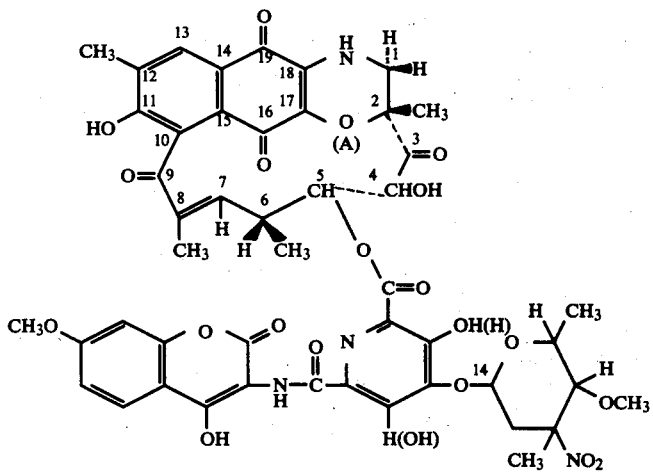

The structure of rubradirin B has been tentatively determined to be as follows:

BRIEF SUMMARY OF THE INVENTION

Upon subjecting rubradirin to base hydrolysis there are obtained novel compounds which can be shown as follows:

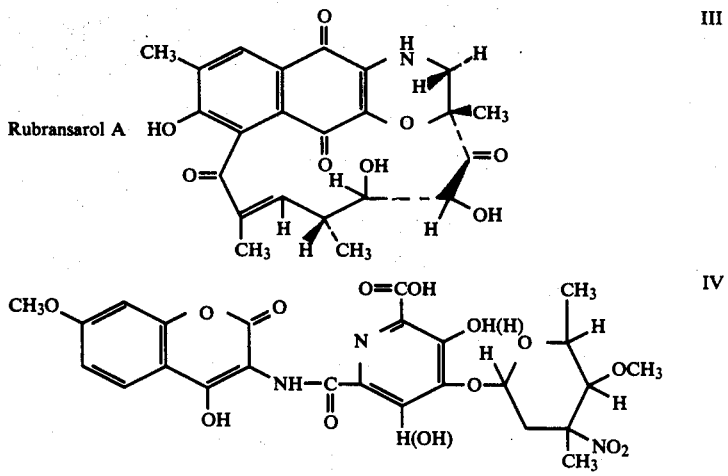

If rubradirin is reacted with an amine, e.g. aqueous methylamine, the amide of IV is obtained.

Acid hydrolysis of rubradirin gives novel compounds which can be shown as follows:

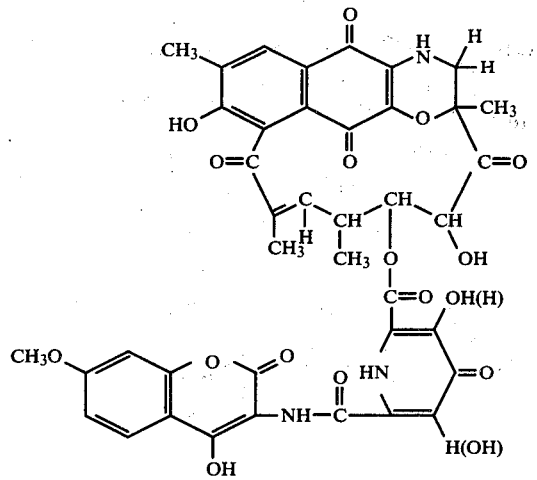

V

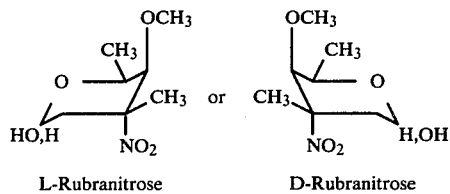

L-Rubranitrose    D-Rubranitrose

VI

Upon reacting compound V with a saturated solution of ammonia and methanol, there are obtained compound III and also another novel compound which can be shown as follows:

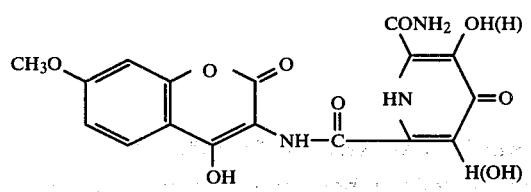

VII

If compound V is reacted with primary amines such as ethylamine, the ethylamide corresponding to VII is obtained.

Degradation of rubradirin in acetic anhydride and pyridine yields a novel compound which can be shown as follows:

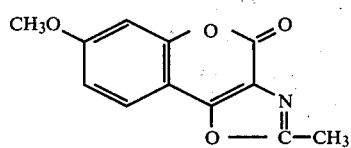

VIII

A similar compound having the structure:

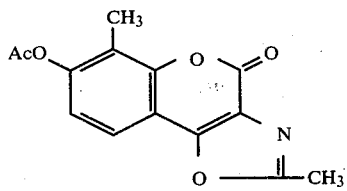

IX wherein Ac is acetyl, is known in the prior art. See U.S. Pat. No. 3,105,088.

Base hydrolysis of rubradirin B gives novel compounds which can be shown as follows:

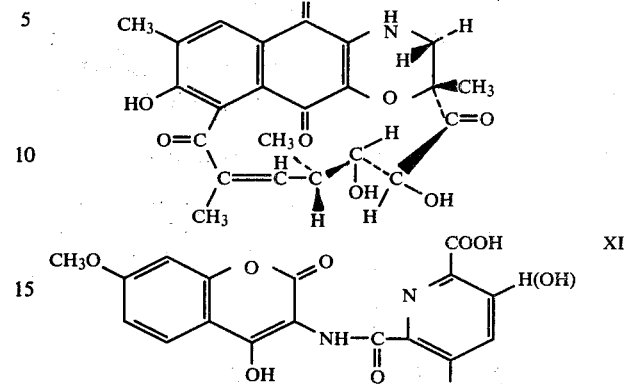

X

XI

DETAILED DESCRIPTION OF THE INVENTION

Upon subjecting rubradirin to base hydrolysis there are obtained compounds III and IV. The reaction can be conducted with ammoniacal, alkali or alkaline earth metal bases, for example, ammonium hydroxide, sodium hydroxide (preferred), potassium hydroxide, and calcium hydroxide. The pH of the reaction, advantageously, is maintained in the range of 10 to about 12.5 for about 36–60 hours, while the temperature is about 20° to about 30° C. The resulting degradation products can be recovered from the reaction mixture by first acidifying the mixture to a pH of about 2.5 with a mineral acid; hydrochloric acid is preferred. The water-insoluble fraction can be extracted with a suitable solvent, for example, chloroform (preferred) or ethyl acetate. The desired products can be precipitated from the solvent extract with Skellysolve B (isomeric hexanes). This material then can be subjected to chromatographic procedures on silica gel to yield compounds III and IV as separate entities. Compound III is active against the bacterium *Sarcina lutea* on a standard agar disc plate assay (80 BU/mg). A biounit (BU) is defined as the concentration of the antibiotic which gives a 20 mm zone of inhibition when 0.08 ml of antibiotic solution is applied to a 12.5 mm diameter adsorbent paper disc. Compound III can be placed into solution for the assay by dissolving in methanol, or acetone, or dimethylformamide and diluting with phosphate buffer at pH 7.8.

Since compound III is active against *S. lutea*, it can be used to swab laboratory benches and equipment in a bacteriology laboratory contaminated with *S. lutea*. Further, it can be used to treat open cooling water systems in which *S. lutea* has been found to be one of the contaminants.

Compounds III and IV can be used as ultraviolet screeners in the plastics industry since they effectively absorb UV rays. For example, they can be used in polyolefin resin formulations for numerous plastic applications to prevent degradation by sunlight.

Acid hydrolysis of rubradirin gives novel compounds V and VI. The hydrolysis can be conducted using acetic acid (preferred) or a mineral acid in about 80% methanol or ethanol. The reaction, advantageously, is maintained at a pH of about 2 to 3 and at a temperature of about 20° to about 30° C. for about 6 days. Filtration of the reaction mixture affords a red crystalline precipitate which is active against *S. lutea* and is identified as compound V. Compound VI can be isolated from the remaining filtrate by first evaporating the filtrate to a residue and then dissolving the residue in chloroform. The chloroform solution, advantageously, can be decolorized by extraction with a 3% aqueous sodium carbonate solution. The dried chloroform solution can be diluted by addition of methanol, followed by evaporation to yield white crystals of compound VI.

Since compound V is active against *S. lutea* (150 BU/mg), it can be used for the same purposes as described above for compound III. It can also be used as an ultraviolet screener, as described above for compounds III and IV.

Compound VI is a stereoisomer of the compound disclosed in JACS, Vol. 90, page 7129 (1968). Compound VI can be used as an intermediate for the preparation of the corresponding amino sugar according to the procedures disclosed in U.S. Pat. No. 3,996,205. Further, the nitro group in compound VI can be reduced to an amine using standard catalytic reduction procedures with Raney nickel or 10% palladium on charcoal. This amine compound can then be used to make antibacterially active antibiotics in accord with the procedures disclosed in U.S. Pat. No. 3,996,205.

Upon reacting compound V with a saturated solution of ammonia and methanol for about 16 hours at about 20° to about 30° C., there are produced compounds III and VII. The reaction mixture can be evaporated to dryness and the residue triturated with a two-phase mixture of chloroform and 0.1 N sulfuric acid. This reaction mixture then can be filtered to give a precipitate containing compound VII. The chloroform phase of the filtrate can be washed, evaporated and dried to yield compound III. Compound VII can be purified from the first precipitate by crystallization from hot methanol.

Compound VII can be used as an ultraviolet screener in the plastics industry, as disclosed above, since it effectively absorbs UV rays.

A mixture of rubradirin, pyridine, and acetic anhydride when refluxed for about 2 to about 4 hours yields compound VIII. This compound can be recovered from the reaction mixture by first pouring the mixture on ice to give a precipitate which can be removed by filtration and recrystallized from methanol twice to give white crystals of compound VIII. Compound VIII also can be used as an ultraviolet screener in the plastics industry since it effectively absorbs UV rays.

Base hydrolysis of rubradirin B yields compounds X and XI. The reaction can be conducted with ammoniacal, alkali or alkaline earth metal bases, for example, ammonium hydroxide, sodium hydroxide (preferred), potassium hydroxide, and calcium hydroxide. The pH of the reaction, advantageously, is maintained in the range of 10 to about 12.5 for about 2 to 3 days. The temperature during this time is maintained at about 20° to about 30° C., preferably at 22° C. These compounds can be recovered from the reaction mixture by first acidifying the mixture to about pH 2 with a mineral acid; sulfuric acid is preferred. The insoluble and chloroform-soluble fractions are pooled. This material can be chromatographed on silica gel 60 to give compound X by elution with chloroform and methanol mixtures. Compound XI can then be isolated from the chromatographic column by elution with methanol.

Compound X is active against *S. lutea* (6 BU/mg) and, thus, can be used to inhibit this bacterium in the same manner as disclosed above for compound III. Further, compound X can be used as an ultraviolet screener in the plastics industry since it effectively absorbs UV rays. Likewise, compound XI can be used as an ultraviolet screener in the plastics industry.

The following examples are illustrative of the process and products of the present invention, but are not to be construed as limiting. All percentages are by weight, and solvent mixture proportions are by volume unless otherwise noted.

EXAMPLE 1—BASE DEGRADATION OF RUBRADIRIN: PREPARATION OF COMPOUND III AND COMPOUND IV

A solution containing 1 g (1 mmol) of rubradirin, 80 mg (2 mmol) of sodium hydroxide and 50 ml of water is stored at room temperature for 42 hours. The pH is 11.5. It is then acidified to pH 2.5 with about 2 ml of 2 N hydrochloric acid and the water-insoluble fraction is taken into chloroform, washed with water and precipitated with Skellysolve B, affording 850 mg of red powder.

This is then chromatographed on pH 5.8-buffered silica gel developed first with chloroform. The first red band, when isolated, consists of 125 mg of unchanged rubradirin. The second red band is found to contain 160 mg of a red powder; base degradation product compound III. Anal. Calcd. for $C_{23}H_{23}NO_8$: N, 3.28; MW 441.1424. Found: N, 3.17; MW 441.1417. Compound III assays 80 BU/mg on a standard disc plate *S. lutea* assay.

The column is then leached with chloroform:methanol (99:1 v/v) which removes some color but minimal solids. A final development with chloroform:methanol (99:5 v/v) removes a brown band which contains 600 mg of light tan crystals; base degradation compound IV. Anal. Calcd. for $C_{25}H_{25}N_3O_{13}$.

EXAMPLE 2—ACID DEGRADATION OF RUBRADIRIN: PREPARATION OF COMPOUND V AND COMPOUND VI

A.

A 2 g quantity of rubradirin in 300 ml of glacial acetic acid is diluted with 100 ml of water and the mixture is stirred at room temperature for 6 days. Filtration affords 1.08 g of compound V, a red crystalline precipitate. This material assays 140 BU/mg (*S. lutea*).

B.

To 3.4 g of rubradirin in 100 ml of glacial acetic acid is added 30 ml of water and the resulting mixture is stirred for 20 days at room temperature. A precipitate (compound V) is isolated by filtration, washed with water and dried; yield, 2.75 g. This compound assays 150 BU/mg vs. *S. lutea*. Anal. Calcd. for $C_{40}H_{33}N_3O_{16}$: C, 59.18; H, 4.10; N, 5.18; MW 811.68. Found: C, 58.27; H, 4.31; N, 4.97; m/e 811.

The filtrate is evaporated in a nitrogen stream. The resulting residue is dissolved in chloroform and this solution is decolorized by extraction with a 3% aqueous sodium carbonate solution. The dried chloroform solution is diluted by addition of 1/5 volume of methanol. This, when partially evaporated, affords a total of 84 mg of white crystals of compound VI in two crops, m.p. 150°–153°. The infrared spectrum of this material shows significant absorbances at 1550, and 1360–1380 cm$^{-1}$.

Anal. Calcd. for $C_8H_{15}NO_5$: C, 46.82; H, 7.37; N, 6.83. Found: C, 46.70; H, 7.63; N, 6.67.

EXAMPLE 3—DEGRADATION OF COMPOUND V

A saturated solution of ammonia and methanol, containing 700 mg of compound V is stirred 16 hours at room temperature, then evaporated to dryness on a rotary evaporator. The residue is triturated with a 2-phase mixture of 200 ml of chloroform and 100 ml of 0.1 N sulfuric acid. This is then filtered, affording a precipitate containing compound VII and a filtrate. The chloroform phase of the filtrate, when washed, evaporated, and dried, yields 280 mg of compound III.

Compound VII is purified from the first precipitate by crystallization from hot methanol; yield, 300 mg.

Anal. Calcd. for $C_{17}H_{13}N_3O_8$: m/e 387. Theory by high resolution MS 387.0702. Found: 387.0702.

EXAMPLE 4—BASE DEGRADATION OF RUBRADIRIN B: PREPARATION OF COMPOUND X AND COMPOUND XI

A suspension of 1 g of rubradirin B in 75 ml of water is brought to pH 11 by addition of 1 N sodium hydroxide solution over the period of 1 hour. After 16 hours the pH is 7.5 and it is then raised and kept at pH 12 for two days by addition of 1 N sodium hydroxide. The solution is acidified to pH 2 with 6 N sulfuric acid and all of the insoluble, and chloroform-soluble fractions are pooled; yield, 700 mg. This material is chromatographed on 100 g of silica gel 60, buffered at pH 5.8 (54.4 g of $KH_2PO_4$/Kg of $SiO_2$) in a column of 3.3 cm diameter. This is eluted with 850 ml of chloroform and these eluates (fractions 1-10) are discarded. Chloroform:methanol, 95:5 v/v is the next eluant and 10-ml fractions are collected (fractions 11-127). Fractions 35-46 are pooled on the basis of tlc (thin layer chromatography) analysis in the system: pH 5.8-buffered silica gel, HF 254: chloroform:methanol (98:2). It displays an $R_f$ of 0.22 vs. 0.32 for the corresponding compound III from rubradirin and 0.66 for starting material rubradirin B.

The product, compound X (180 mg), which subsequently crystallizes from deutero-chloroform, assays at 6 BU/mg (S. lutea). $[\alpha]_D = +108°$ (c, 0.02, acetone). Anal. Calcd. for $C_{23}H_{23}N_1O_8$: m/e 441, Theory 441.1424. Found: 441.1413.

Compound XI is eluted from the above column with methanol and isolated by evaporation.

EXAMPLE 5—DEGRADATION OF RUBRADIRIN IN ACETIC ANHYDRIDE AND PYRIDINE: PREPARATION OF COMPOUND VIII

A mixture of 10 g of rubradirin, 125 ml of pyridine, and 25 g of acetic anhydride is refluxed for 4 hours. It is then poured on ice and the resulting precipitate is removed by filtration and recrystallized from methanol twice to give 300 mg of white crystals of compound VIII, mp 212°-213°.

Anal. Calcd. for $C_{12}H_9NO_4$: C, 62.34; H, 3.92; N, 6.06. Found: C, 62.49; H, 3.78; N, 6.05.

EXAMPLE 6

By substituting rubradirin B, or compound IV, or compound V, or compound VII, or compound XI, for rubradirin in Example 5, there is obtained compound VIII.

Rubradirin B can be prepared as follows:

A. Fermentation

An agar slant of *Streptomyces achromogenes* var. *rubradiris*, NRRL 3061 *, is used to inoculate a series of 500-ml Erlenmeyer flasks each containing 100 ml of sterile seed medium consisting of the following ingredients:

| | |
|---|---|
| Glucose monohydrate | 25 g/liter |
| Pharmamedia** | 40 g/liter |
| Tap water q.s. | 1 liter |

*This microorganism is known and available from the culture repository at Peoria, Illinois, upon request.
**Pharmamedia is an industrial grade of cottonseed flour produced by Traders Oil Mill Company, Fort Worth, Texas.

* This microorganism is known and available from the culture repository at Peoria, Illinois, upon request.
** Pharmamedia is an industrial grade of cottonseed flour produced by Traders Oil Mill Company, Fort Worth, Texas.

The flasks are incubated for 3 days at 28° C. on a Gump rotary shaker operating at 250 r.p.m.

Seed inoculum (5%), prepared as described above, is used to inoculate a series of 500-ml Erlenmeyer flasks each containing 100 ml of sterile fermentation medium consisting of the following ingredients:

| | |
|---|---|
| Starch | 10 g/liter |
| Corn steep liquor | 20 g/liter |
| Distillers' solubles | 15 g/liter |
| Mg $(NO_3)_2 \cdot 6H_2O$ | 3.8 g/liter |
| Tap water q.s. | 1 liter |

The fermentation medium presterilization pH is 7.2.

The fermentation flasks are incubated at 28° C. on a Gump rotary shaker operating at 250 r.p.m. The fermentation flasks are harvested after about 3 to 4 days. A typical shake flask fermentation is depicted below. The assay is against the microorganism *S. lutea*. It is a disc plate assay using 0.1 M phosphate buffer, pH 7.85, as diluent.

| Day | Assay, Biounit/ml |
|---|---|
| 1 | trace |
| 2 | 104 |
| 3 | 160 |
| 4 | 64 |

NOTE:
One Biounit corresponds to the dilution factor of the sample to yield an inhibition zone of 20 mm.

B. Recovery

Whole broth from a fermentation, as described above, is slurried with 4 percent of its weight of diatomaceous earth and filtered. The filter cake is washed with 1/10 volume of water and the wash is added to the clear beer. The clear beer is adjusted to pH 4.0 with 6 N sulfuric acid and filtered with the aid of diatomaceous earth. The spent beer is discarded. The wet cake is leached with ethyl acetate and the solvent phase is then concentrated to an aqueous phase. The latter is freeze-dried. The residue is dissolved in ethyl acetate and diluted with 4 volumes of Skellysolve B. The precipitate which is collected and dried contains a mixture including rubradirin and rubradirin B.

C. Purification

A one gram quantity of crude preparation containing rubradirin B, prepared as described above, is chromatographed on 500 g of silica gel G (70-230 mesh, E.

Merck), buffered at pH 5.8. The first elution with 1500 ml of chloroform is discarded. Thereafter 20 ml fractions are collected. Tubes 201 to 470 contain rubradirin by tlc. The elution solvent is changed to chloroform-:methanol (97:3). Tubes 471–510 contain a mixture of rubradirin and rubradirin B. The solids in this fraction are isolated by concentration and precipitation in Skellysolve B, 310 mg.

The combined solids from the above chromatography and two similar ones, 660 mg total, are then dissolved and suspended in 30 ml of chloroform, and this is stirred for 1 hour and filtered. The semicrystalline precipitate, 160 mg, is found to be essentially pure rubradirin B by tlc.

The tlc is run on Eastman silica gel (#6060) sheets with the solvent system ethyl acetate-acetone-water (8:5:1) and bioautographed on trays seeded with *S. lutea*. Approximately 0.5 γ of line product preparations and correspondingly lesser amounts of higher purity preparations are applied for analyses.

Preparations are assayed after they have been adjusted to pH 3.0 and dried in vacuum. Dilutions are made in methanol and a quantity of 0.08 ml is applied to 12.7 mm assay discs which are dried and placed on agar trays seeded with *S. lutea*. Assays are expressed as biounits.

Salts of the compounds of the subject invention, except compound VI, are formed employing the free acid and an inorganic or organic base. The salts can be prepared as for example by suspending the free acid in water, adding a dilute base until the pH of the mixture is about 7 to 8, and freeze-drying the mixture to provide a dried residue consisting of the salt. Salts which can be formed include the sodium, potassium, and calcium. Other salts including those with organic bases such as primary, secondary, and tertiary mono-, di-, and polyamines can also be formed using the above-described or other commonly employed procedures. The salts can be used for the same purposes as the parent free acid.

The compounds of the subject invention can be acylated under standard acylating conditions with an appropriate acid halide or anhydride to give the acylated compounds. For example, compounds III and X can be acylated at positions 4, 5 and 11 to give the triacylate of said compounds. Compound V can be acylated at positions 4 and 11 of the Ansa moiety and at the free hydroxyl at position 3 of the nitro-sugar moiety. Compound VI can be acylated on the anomeric carbon. Compounds IV and XI can be esterified with diazomethane or lower alcohols (1 to 4 carbon atoms, inclusive) under acid catalysis to form esters. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and lower alkoxy-hydrocarbon carboxylic acids include hydrocarbon carboxylic acids as given above which are substituted by one or more of halogen, nitro, hydroxy, amino, cyano, or thiocyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methylcyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcyclic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
and the like.

The acylated compounds, amides and esters, as described herein, can be used for the same purposes as disclosed for the parent compounds. Additionally, the acylates can be used to upgrade the parent compound, i.e. the parent compound is acylated, then deacylated

EXAMPLE 7—ETHYLAMIDE OF COMPOUND IV

A solution containing 700 mg of rubradirin in 20 ml of 30% aqueous ethylamine is stored at room temperature for 36 hours, then evaporated to dryness on a rotary evaporator. The residue is redissolved in 20 ml of water, brought to pH 1.5 with 2N HCl, and extracted with a total of 40 ml of chloroform in several batches. The extract is concentrated to a residue (520 mg) which is chromatographed over 125 g of pH 5.8-buffered silica gel in a 3 cm (dia.) column developed by chloroform-:methanol (98:2). The residue from fractions (20 ml) 50–70, 110 mg, is identified as rubransarol A. The residue from fractions 41–45 (200 mg) is crystallized from a chloroform and butanone mixture to give the title compound: 170 mg, M. 209° dec. Anal. Calcd. for $C_{27}H_{30}N_4O_{12}$: C, 53.82; H, 5.02; N, 9.30. Found: C, 53.05; H, 5.11; N, 9.13.

EXAMPLE 8—METHYLAMIDE OF COMPOUND IV

A 7 g quantity of rubradirin, dissolved in 100 ml of 40% aqueous methylamine, is stored at room temperature for 20 hours. It is then concentrated to 25 ml on a rotary evaporator and brought to pH 2 with 2N hydrochloric acid. The precipitate, after collection and drying, is suspended in methyl ethyl ketone affording pale yellow crystals of the title compound: 3.7 g (94%), M. 265° dec. This material has two titratable groups, $PK_{3}$· 5.3 and 7.8 in 85% aqueous dimethyl sulfoxide. Anal. Calcd. for $C_{26}H_{28}N_4O_{12}$: C, 53.06; H, 4.80; N, 9.52; M.W. 588. Found: C, 53.08; H, 4.88; N, 9.34; M+ 588.

EXAMPLE 9—ETHYLAMIDE OF COMPOUND XI

Rubradirin B (1 g, 1.25 mmol) is dissolved in 20 ml of 30% aqueous ethylamine and stored 16 hours at room temperature. It is then evaporated to a solid residue on a rotary evaporator and to this is added a mixture of 20 ml of 0.2N HCl, 20 ml of chloroform, and 20 ml of acetone. Following filtration, the precipitate is washed thoroughly with acetone, leaving 450 mg of yellow solid. Recrystallization from boiling dioxane afforded 170 mg of pale yellow crystals of the title compound: M. >285°. Anal. Calcd. for $C_{19}H_{17}N_3O_7$: C, 57.14; H, 4.29; N, 10.52; M.W. (High resolution mass spectroscopy) 399.10664. Found: C, 56.84; H, 4.34; N, 10.49; M.W., 399.10733.

I claim:

1. A compound which can be shown by the following structural formula:

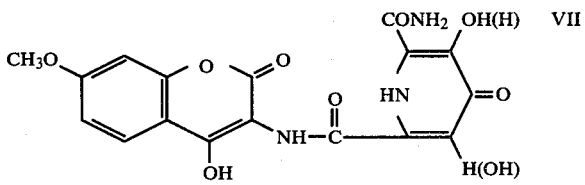

and its base salts.

2. Acylates of the compound defined in claim 1 wherein said acyl group consists of a hydrocarbon carboxylic acid acyl of from 2 to 18 carbon atoms, inclusive: halo-, nitro-, hydroxy-, amino-, cyano-, thiocyano-, and lower alkoxy-substituted hydrocarbon carboxylic acid acyl of from 2 to 18 carbon atoms, inclusive.

* * * * *

UNITED STATES PATENT AND TRADEMARK OFFICE
CERTIFICATE OF CORRECTION

PATENT NO. : 4,154,938
DATED : May 15, 1979
INVENTOR(S) : Herman Hoeksema

It is certified that error appears in the above-identified patent and that said Letters Patent are hereby corrected as shown below:

Column 2, structure II, lines 10-11, for

"    O              "    read --    O
                                      \
      C=O                              C=O                --.

Column 8, lines 15-18, for "* This microorganism is known and available from the culture repository at Peoria, Illinois, upon request.  ** Pharmamedia is an industrial grade of cottonseed flour produced by Traders Oil Mill Company, Fort Worth, Texas." should be deleted.
Column 9, line 60, for "caprioc" read -- caproic --.
Column 11, line 33, for "$PK_3$" read -- $PK_a$ --.

Signed and Sealed this

Second Day of October 1979

[SEAL]

Attest:

RUTH C. MASON
Attesting Officer

LUTRELLE F. PARKER
Acting Commissioner of Patents and Trademarks